US007731981B2

(12) United States Patent
Trieu et al.

(10) Patent No.: US 7,731,981 B2
(45) Date of Patent: Jun. 8, 2010

(54) COLLAGEN-BASED MATERIALS AND METHODS FOR TREATING SYNOVIAL JOINTS

(75) Inventors: Hai H. Trieu, Cordova, TN (US); Michael C. Sherman, Memphis, TN (US)

(73) Assignee: Warsaw Orthopedic, Inc.

( * ) Notice: Subject to any disclaimer, the term of this patent is extended or adjusted under 35 U.S.C. 154(b) by 323 days.

(21) Appl. No.: 11/626,147

(22) Filed: Jan. 23, 2007

(65) Prior Publication Data
US 2007/0134343 A1 Jun. 14, 2007

Related U.S. Application Data

(62) Division of application No. 10/704,167, filed on Nov. 7, 2003, now abandoned.

(60) Provisional application No. 60/426,613, filed on Nov. 15, 2002.

(51) Int. Cl.
*A61K 9/00* (2006.01)
(52) U.S. Cl. ..................................................... 424/400
(58) Field of Classification Search .................. 424/400
See application file for complete search history.

(56) References Cited

U.S. PATENT DOCUMENTS

| | | |
|---|---|---|
| 3,551,560 A | 12/1970 | Thiele |
| 3,855,638 A | 12/1974 | Pillar |
| 3,875,595 A | 4/1975 | Froning |
| 4,060,081 A | 11/1977 | Yannas et al. |
| 4,085,466 A | 4/1978 | Goodfellow et al. |
| 4,185,813 A | 1/1980 | Spann |
| 4,280,954 A | 7/1981 | Yannas et al. |
| 4,344,193 A | 8/1982 | Kenny |
| 4,349,921 A | 9/1982 | Kuntz |
| 4,350,629 A | 9/1982 | Yannas et al. |
| 4,378,224 A | 3/1983 | Nimni et al. |
| 4,400,833 A | 8/1983 | Kurland |
| 4,418,691 A | 12/1983 | Yannas et al. |
| 4,424,208 A | 1/1984 | Wallace et al. |
| 4,448,718 A | 5/1984 | Yannas et al. |
| 4,458,678 A | 7/1984 | Yannas et al. |
| 4,505,266 A | 3/1985 | Yannas et al. |
| 4,544,516 A | 10/1985 | Hughes et al. |
| 4,578,079 A | 3/1986 | Ruoslahti et al. |
| 4,582,640 A | 4/1986 | Smestad et al. |
| 4,589,881 A | 5/1986 | Pierschbacher et al. |
| 4,614,794 A | 9/1986 | Easton et al. |
| 4,627,853 A | 12/1986 | Campbell et al. |
| 4,642,117 A | 2/1987 | Nguyen et al. |
| 4,642,120 A | 2/1987 | Nevo et al. |
| 4,661,111 A | 4/1987 | Ruoslahti et al. |
| 4,703,108 A | 10/1987 | Silver et al. |
| 4,772,287 A | 9/1988 | Ray et al. |
| 4,787,900 A | 11/1988 | Yannas |
| 4,801,299 A | 1/1989 | Brendel et al. |
| 4,803,075 A | 2/1989 | Wallace et al. |
| 4,837,285 A | 6/1989 | Berg et al. |
| 4,879,135 A | 11/1989 | Greco et al. |
| 4,880,492 A | 11/1989 | Erdmann et al. |
| 4,904,260 A | 2/1990 | Ray et al. |
| 4,946,792 A | 8/1990 | O'Leary |
| 4,976,733 A | 12/1990 | Giradot |
| 5,007,934 A | 4/1991 | Stone |
| 5,067,962 A | 11/1991 | Campbell et al. |
| 5,106,949 A | 4/1992 | Kemp et al. |
| 5,108,438 A | 4/1992 | Stone |
| 5,137,514 A | 8/1992 | Ryan |
| 5,192,326 A | 3/1993 | Bao et al. |
| 5,229,497 A | 7/1993 | Boni |
| 5,258,043 A | 11/1993 | Stone |
| 5,397,352 A | 3/1995 | Burres |
| 5,478,739 A | 12/1995 | Slivka et al. |
| 5,507,810 A | 4/1996 | Prewett et al. |
| 5,549,679 A | 8/1996 | Kuslich |
| 5,562,736 A | 10/1996 | Ray et al. |
| 5,571,189 A | 11/1996 | Kuslich |
| 5,607,476 A | 3/1997 | Prewett et al. |
| 5,713,959 A | 2/1998 | Bartlett et al. |
| 5,733,337 A | 3/1998 | Carr, Jr. et al. |
| 5,788,625 A | 8/1998 | Plouhar et al. |
| 5,827,289 A | 10/1998 | Reiley et al. |
| 5,858,747 A | 1/1999 | Schinstine et al. |
| 5,888,220 A | 3/1999 | Felt et al. |
| 5,894,070 A | 4/1999 | Hansson et al. |
| 5,916,870 A | 6/1999 | Lee et al. |
| 5,922,028 A | 7/1999 | Plouhar et al. |
| 5,935,849 A | 8/1999 | Schinstine et al. |
| 5,948,428 A | 9/1999 | Lee et al. |
| 5,964,807 A | 10/1999 | Gan et al. |
| 5,976,186 A | 11/1999 | Bao et al. |
| 5,980,504 A | 11/1999 | Sharkey et al. |
| 5,994,325 A | 11/1999 | Roufa et al. |
| 6,007,570 A | 12/1999 | Sharkey et al. |
| 6,022,376 A | 2/2000 | Assell et al. |
| 6,025,538 A | 2/2000 | Yaccarino, III |

(Continued)

FOREIGN PATENT DOCUMENTS

DE 19959975 A1 7/2001

(Continued)

OTHER PUBLICATIONS

Tay, B.K., et al., "Use of a Collagen-Hydroxyapatite Matrix in Spinal Fusion. A Rabbit Model," Spine, vol. 23, No. 21, pp. 2276-2281, Nov. 1, 1998.

(Continued)

*Primary Examiner*—Ruth A Davis

(57) ABSTRACT

A method of treating a synovial joint by injecting particles of collagen-based material into the joint. The particles may be dehydrated before implantation, and rehydrated after implantation, or they may be implanted in a "wet" state—such as a slurry or gel. Radiocontrast materials may be included to enhance imaging of the injected material. Other additives may include analgesics, antibiotics, proteoglycans, growth factors, and/or other cells effective to promote healing and/or proper joint function.

10 Claims, 6 Drawing Sheets

U.S. PATENT DOCUMENTS

| | | |
|---|---|---|
| 6,027,743 A * | 2/2000 | Khouri et al. .......... 424/423 |
| 6,046,379 A | 4/2000 | Stone et al. |
| 6,066,154 A | 5/2000 | Reiley et al. |
| 6,073,051 A | 6/2000 | Sharkey et al. |
| 6,077,989 A | 6/2000 | Kandel et al. |
| 6,080,194 A | 6/2000 | Pachence et al. |
| 6,080,579 A | 6/2000 | Hanley, Jr. et al. |
| 6,095,149 A | 8/2000 | Sharkey et al. |
| 6,099,514 A | 8/2000 | Sharkey et al. |
| 6,122,549 A | 9/2000 | Sharkey et al. |
| 6,123,731 A | 9/2000 | Boyce et al. |
| 6,126,682 A | 10/2000 | Sharkey et al. |
| 6,140,452 A | 10/2000 | Felt et al. |
| 6,146,422 A | 11/2000 | Lawson |
| 6,165,489 A | 12/2000 | Berg et al. |
| 6,176,880 B1 | 1/2001 | Plouhar et al. |
| 6,179,872 B1 | 1/2001 | Bell et al. |
| 6,197,061 B1 | 3/2001 | Masuda et al. |
| 6,224,630 B1 | 5/2001 | Bao et al. |
| 6,235,043 B1 | 5/2001 | Reiley et al. |
| 6,240,926 B1 | 6/2001 | Chin Gan et al. |
| 6,248,110 B1 | 6/2001 | Reiley et al. |
| 6,248,131 B1 | 6/2001 | Felt et al. |
| 6,261,311 B1 | 7/2001 | Sharkey et al. |
| 6,264,659 B1 | 7/2001 | Ross et al. |
| 6,264,695 B1 | 7/2001 | Stoy |
| 6,290,715 B1 | 9/2001 | Sharkey et al. |
| 6,306,169 B1 | 10/2001 | Lee et al. |
| 6,306,177 B1 | 10/2001 | Felt et al. |
| 6,322,786 B1 | 11/2001 | Anderson |
| 6,324,710 B1 | 12/2001 | Hernandez et al. |
| 6,340,369 B1 | 1/2002 | Ferree |
| 6,344,058 B1 | 2/2002 | Ferree |
| 6,352,557 B1 | 3/2002 | Ferree |
| 6,352,558 B1 | 3/2002 | Spector |
| 6,402,784 B1 | 6/2002 | Wardlaw |
| 6,419,702 B1 | 7/2002 | Ferree |
| 6,423,083 B2 | 7/2002 | Reiley et al. |
| 6,425,919 B1 | 7/2002 | Lambrecht |
| 6,428,576 B1 | 8/2002 | Haldimann |
| 6,436,119 B1 | 8/2002 | Erb et al. |
| 6,443,988 B2 | 9/2002 | Felt et al. |
| 6,482,235 B1 | 11/2002 | Lambrecht et al. |
| 6,592,625 B2 | 7/2003 | Cauthen |
| 6,623,963 B1 | 9/2003 | Muller et al. |
| 6,641,587 B2 | 11/2003 | Scribner et al. |
| 6,648,918 B2 | 11/2003 | Ferree |
| 6,662,805 B2 | 12/2003 | Frondoza et al. |
| 6,699,294 B2 | 3/2004 | Urry |
| 6,712,853 B2 | 3/2004 | Kuslich |
| 6,716,251 B1 | 4/2004 | Asius et al. |
| 6,723,335 B1 | 4/2004 | Moehlenbruck et al. |
| 6,726,691 B2 | 4/2004 | Osorio et al. |
| 6,783,546 B2 | 8/2004 | Zucherman et al. |
| 6,793,677 B2 | 9/2004 | Ferree |
| 6,827,716 B2 | 12/2004 | Ryan et al. |
| 6,929,640 B1 | 8/2005 | Underwood et al. |
| 6,932,843 B2 | 8/2005 | Smith et al. |
| 6,936,072 B2 | 8/2005 | Lambrecht et al. |
| 6,939,329 B1 | 9/2005 | Verkaart |
| 6,958,077 B2 | 10/2005 | Suddaby |
| 6,969,404 B2 | 11/2005 | Ferree |
| 6,980,862 B2 | 12/2005 | Fredricks et al. |
| 7,001,431 B2 | 2/2006 | Bao et al. |
| 7,060,103 B2 | 6/2006 | Carr, Jr. et al. |
| 7,077,865 B2 | 7/2006 | Bao et al. |
| 2001/0004710 A1 | 6/2001 | Felt et al. |
| 2001/0006948 A1 | 7/2001 | Kang et al. |
| 2001/0011174 A1 | 8/2001 | Reiley et al. |
| 2001/0016195 A1 | 8/2001 | Tobinick et al. |
| 2001/0016772 A1 | 8/2001 | Lee et al. |
| 2001/0020476 A1 | 9/2001 | Gan et al. |
| 2001/0024823 A1 | 9/2001 | Vukicevik et al. |
| 2001/0027199 A1 | 10/2001 | Olmarker |
| 2001/0049527 A1 | 12/2001 | Cragg |
| 2001/0049531 A1 | 12/2001 | Reiley et al. |
| 2001/0051834 A1 | 12/2001 | Frondoza et al. |
| 2001/0055594 A1 | 12/2001 | Olmarker et al. |
| 2002/0016583 A1 | 2/2002 | Cragg |
| 2002/0026195 A1 | 2/2002 | Layne et al. |
| 2002/0029083 A1 | 3/2002 | Zucherman et al. |
| 2002/0032155 A1 | 3/2002 | Ferree |
| 2002/0038150 A1 | 3/2002 | Urry |
| 2002/0045942 A1 | 4/2002 | Ham |
| 2002/0049498 A1 | 4/2002 | Yuksel et al. |
| 2002/0055143 A1 | 5/2002 | Bell et al. |
| 2002/0068974 A1 | 6/2002 | Kuslich et al. |
| 2002/0068975 A1 | 6/2002 | Teitelbaum et al. |
| 2002/0082608 A1 | 6/2002 | Reiley et al. |
| 2002/0115742 A1 | 8/2002 | Trieu et al. |
| 2002/0116069 A1 | 8/2002 | Urry |
| 2002/0120347 A1 | 8/2002 | Boyer, II et al. |
| 2002/0133231 A1 | 9/2002 | Ferree |
| 2002/0151979 A1 | 10/2002 | Lambrecht et al. |
| 2002/0176893 A1 | 11/2002 | Wironen et al. |
| 2002/0177866 A1 | 11/2002 | Weikel et al. |
| 2003/0008817 A1 | 1/2003 | Sander |
| 2003/0104026 A1 | 6/2003 | Wironen et al. |
| 2003/0130664 A1 | 7/2003 | Boucher et al. |
| 2003/0158607 A1 | 8/2003 | Carr et al. |
| 2004/0010251 A1 | 1/2004 | Pitaru et al. |
| 2004/0024081 A1 | 2/2004 | Trieu et al. |
| 2004/0030392 A1 | 2/2004 | Lambrecht et al. |
| 2004/0034429 A1 | 2/2004 | Lambrecht et al. |
| 2004/0054414 A1 | 3/2004 | Trieu et al. |
| 2004/0064023 A1 | 4/2004 | Ryan et al. |
| 2004/0073308 A1 | 4/2004 | Kuslich et al. |
| 2004/0083001 A1 | 4/2004 | Kandel |
| 2004/0083002 A1 | 4/2004 | Belef et al. |
| 2004/0091540 A1 | 5/2004 | Desrosier et al. |
| 2004/0092946 A1 | 5/2004 | Bagga et al. |
| 2004/0101959 A1 | 5/2004 | Marko et al. |
| 2004/0172132 A1 | 9/2004 | Ginn |
| 2004/0186471 A1 | 9/2004 | Trieu |
| 2004/0220101 A1 | 11/2004 | Ferree |
| 2004/0220102 A1 | 11/2004 | Ferree |
| 2004/0228901 A1 | 11/2004 | Trieu et al. |
| 2004/0229786 A1 | 11/2004 | Attawia et al. |
| 2004/0260397 A1 | 12/2004 | Lambrecht et al. |
| 2005/0002909 A1 | 1/2005 | Moehlenbruck et al. |
| 2005/0055094 A1 | 3/2005 | Kuislich |
| 2005/0069571 A1 | 3/2005 | Slivka et al. |
| 2005/0070915 A1 | 3/2005 | Mazzuca et al. |
| 2005/0090901 A1 | 4/2005 | Studer |
| 2005/0100538 A1 | 5/2005 | Mohamed et al. |
| 2005/0102030 A1 | 5/2005 | Yuksel et al. |
| 2005/0113923 A1 | 5/2005 | Acker et al. |
| 2005/0118228 A1 | 6/2005 | Trieu et al. |
| 2005/0119750 A1 | 6/2005 | Studer |
| 2005/0119754 A1 | 6/2005 | Trieu et al. |
| 2005/0125066 A1 | 6/2005 | McAfee |
| 2005/0131540 A1 | 6/2005 | Trieu |
| 2005/0131541 A1 | 6/2005 | Trieu |
| 2005/0143688 A1 | 6/2005 | Lin et al. |
| 2005/0149007 A1 | 7/2005 | Carl |
| 2005/0149046 A1 | 7/2005 | Friedman et al. |
| 2005/0149197 A1 | 7/2005 | Cauthen |
| 2005/0152986 A1 | 7/2005 | Duneas et al. |
| 2005/0154463 A1 | 7/2005 | Trieu |
| 2005/0159817 A1 | 7/2005 | Ferree |
| 2005/0177168 A1 | 8/2005 | Brunnett et al. |
| 2005/0182414 A1 | 8/2005 | Manzi et al. |
| 2005/0182418 A1 | 8/2005 | Boyd et al. |
| 2005/0186673 A1 | 8/2005 | Geistlich et al. |

| | | | |
|---|---|---|---|
| 2005/0187543 A1 | 8/2005 | Underwood et al. |
| 2005/0187556 A1 | 8/2005 | Stack et al. |
| 2005/0191331 A1 | 9/2005 | Hunter et al. |
| 2005/0196387 A1 | 9/2005 | Seyedin et al. |
| 2005/0197707 A1 | 9/2005 | Trieu et al. |
| 2005/0203206 A1 | 9/2005 | Trieu |
| 2005/0203527 A1 | 9/2005 | Carrison et al. |
| 2005/0203537 A1 | 9/2005 | Wiley et al. |
| 2005/0209595 A1 | 9/2005 | Karmon |
| 2005/0209601 A1 | 9/2005 | Bowman et al. |
| 2005/0209602 A1 | 9/2005 | Bowman et al. |
| 2005/0222538 A1 | 10/2005 | Embry et al. |
| 2005/0222684 A1 | 10/2005 | Ferree |
| 2005/0234493 A1 | 10/2005 | Carr et al. |
| 2005/0234498 A1 | 10/2005 | Gronemeyer et al. |
| 2005/0234557 A1 | 10/2005 | Lambrecht et al. |
| 2005/0240171 A1 | 10/2005 | Forrest |
| 2005/0251259 A1 | 11/2005 | Suddaby |
| 2005/0256580 A1 | 11/2005 | Marissen |
| 2005/0261684 A1 | 11/2005 | Shaolian et al. |
| 2005/0267580 A1 | 12/2005 | Suddaby |
| 2005/0267583 A1 | 12/2005 | Higham et al. |
| 2005/0273093 A1 | 12/2005 | Patel et al. |
| 2005/0277996 A1 | 12/2005 | Podhajsky |
| 2006/0019869 A1 | 1/2006 | Thomas et al. |
| 2006/0044561 A1 | 3/2006 | Nii |
| 2006/0196387 A1 | 9/2006 | Hartley et al. |
| 2007/0026053 A1 | 2/2007 | Pedrozo et al. |

FOREIGN PATENT DOCUMENTS

| | | |
|---|---|---|
| EP | 0305028 | 3/1984 |
| EP | 0277678 | 10/1988 |
| EP | 0747067 A2 | 12/1996 |
| EP | 1313412 A2 | 5/2003 |
| EP | 1407729 A1 | 4/2004 |
| EP | 1421957 A1 | 5/2004 |
| EP | 1328222 B1 | 3/2005 |
| EP | 1214026 B1 | 4/2005 |
| EP | 1198209 B1 | 5/2005 |
| EP | 1582166 A2 | 5/2005 |
| EP | 1051207 B1 | 8/2005 |
| EP | 1563808 A1 | 8/2005 |
| EP | 1563809 A2 | 8/2005 |
| EP | 15754548 A1 | 9/2005 |
| GB | 01515963 | 6/1978 |
| GB | 2407580 A | 5/2005 |
| JP | 2005103296 A | 4/2005 |
| JP | 2005118436 A | 5/2005 |
| JP | 2005152501 A | 6/2005 |
| WO | WO 8910728 | 11/1989 |
| WO | WO 99/04720 A1 | 2/1992 |
| WO | 9210982 A1 | 7/1992 |
| WO | 9611642 A1 | 4/1996 |
| WO | WO 97/22371 A1 | 6/1997 |
| WO | WO 99/43271 | 9/1999 |
| WO | 9959669 A1 | 11/1999 |
| WO | 9961084 A1 | 12/1999 |
| WO | 9962439 A1 | 12/1999 |
| WO | WO 02/40070 A2 | 5/2000 |
| WO | 0034556 A1 | 6/2000 |
| WO | WO 00/62832 A1 | 10/2000 |
| WO | WO 00/75659 A1 | 12/2000 |
| WO | WO 01/76654 A1 | 10/2001 |
| WO | 0217825 A2 | 3/2002 |
| WO | WO 02/054978 A2 | 7/2002 |
| WO | WO 02/000142 A2 | 10/2002 |
| WO | 03011155 A2 | 2/2003 |
| WO | 03066120 A1 | 8/2003 |
| WO | 03099230 A2 | 12/2003 |
| WO | 2004002375 A1 | 1/2004 |
| WO | 2004022155 A2 | 3/2004 |
| WO | 2004026190 A2 | 4/2004 |
| WO | 2004028414 A1 | 4/2004 |
| WO | 2004030548 A1 | 4/2004 |
| WO | 2004032808 A2 | 4/2004 |
| WO | WO 2004/026189 A2 | 4/2004 |
| WO | 2004041075 A2 | 5/2004 |
| WO | 2004045667 A1 | 6/2004 |
| WO | WO 2004/045667 A1 | 6/2004 |
| WO | 2004060425 A2 | 7/2004 |
| WO | 2004064673 A2 | 8/2004 |
| WO | 2004069296 A1 | 8/2004 |
| WO | 2004073532 A1 | 9/2004 |
| WO | 2004073563 A2 | 9/2004 |
| WO | 2004093934 A2 | 11/2004 |
| WO | WO 2004/093934 A2 | 11/2004 |
| WO | 2005000283 A2 | 1/2005 |
| WO | 2005004755 A1 | 1/2005 |
| WO | 2005032424 A1 | 4/2005 |
| WO | 2005034781 A1 | 4/2005 |
| WO | 2005034800 A2 | 4/2005 |
| WO | 2005041813 A2 | 5/2005 |
| WO | 2005049055 A1 | 6/2005 |
| WO | 2005063316 A1 | 7/2005 |
| WO | 2005070071 A2 | 8/2005 |
| WO | 2005070439 A1 | 8/2005 |
| WO | 2005081870 A2 | 9/2005 |
| WO | 2005092248 A1 | 10/2005 |
| WO | 2005092249 A1 | 10/2005 |
| WO | 2005096978 A1 | 10/2005 |
| WO | 2005099392 A2 | 10/2005 |
| WO | 2005102433 A2 | 11/2005 |
| WO | 2005102440 A2 | 11/2005 |
| WO | 2005105168 A1 | 11/2005 |
| WO | 2005107827 A1 | 11/2005 |
| WO | 2005113032 A2 | 12/2005 |
| WO | 2005118015 A1 | 12/2005 |
| WO | 2006002417 A2 | 1/2006 |
| WO | 2006138098 A1 | 12/2006 |

OTHER PUBLICATIONS

Burres, S., "Fascian," Facial Plast Surg, vol. 20, No. 2, pp. 149-152, May 2004.
Burres, S., "Midface Volume Replacement with a Transmaxiallary Implant," Aesthetic Plast Surg, vol. 29, No. 1, pp. 1-4, Jan.-Feb. 2005.
Burres, S., "Soft-tissue augmentation with fascian," Clin Plast Surg, vol. 28, No. 1, pp. 101-110, Jan. 2001. Abstract Only.
Burres, S., "Preserved Participate Fascia Lata for Injection: A New Alternative," vol. 25, No. 10, pp. 790-794, Oct. 1999.
"Fascia & Fascian" http://fascian.com/fascian.htm, Apr. 25, 2003, 9 pgs.
Burres, S., "Intralingual Injection of Particulate Fascia for Tongue Paralysis," Rhinological and Otological Society, Inc., The Laryngoscope, vol. 114, pp. 1204-1205, Jul. 2004.
Shore, J. W., "Injectable Lyophilized Particulate Human Fascia Lata (Fascian) for Lip, Perioral, and Glabellar Enhancement," Ophthalmic Plastic and Reconstructive Surgery, vol. 16, No. 1, pp. 23-27, Jan. 2000.
Images 1 and 2.
FASCIAN-Printout from website: fascian.com, Jul. 21, 2008.

* cited by examiner

COLLAGEN-BASED MATERIALS AND METHODS FOR TREATING SYNOVIAL JOINTS

REFERENCE TO RELATED APPLICATIONS

This application is a Divisional of U.S. patent application Ser. No. 10/704,167, filed Nov. 7, 2003, now abandoned, which claims the benefit of U.S. Provisional Patent Application No. 60/426,613, filed Nov. 15, 2002, which are hereby incorporated by reference.

FIELD OF THE INVENTION

The present invention relates generally to materials and methods for treating synovial joints, and more particularly to materials and methods for augmenting synovial joints with collagen-based materials.

BACKGROUND OF THE INVENTION

Synovial joints are the most common joints of the mammalian appendicular skeleton, representing highly evolved, movable joints. A typical synovial joint comprises two bone ends covered by layer of articular cartilage. The cartilage is smooth and resilient, and facilitates low-friction movement of the bones in the joint.

The bone ends and associated cartilage are surrounded by a joint capsule—a "sack" of membrane that produces synovial fluid. The capsule and fluid protect and support the cartilage and connective tissue, carrying nutrients to the articular cartilage and removing the metabolic wastes.

The articular cartilage is a thin (2-3 mm) layer of hyaline cartilage on the epiphysis of the bone. It lacks a perichondrium, and thus has a limited capacity for repair when damaged. Additionally, the natural aging process can cause the articular cartilage to degenerate somewhat, reducing its capacity to protect and cushion the bone ends.

Zygapophysial joints, better known as facet joints, are the mechanism by which each vertebra of the spine connects to the vertebra above and/or below it. Each joint comprises two facet bones—an inferior facet and a superior facet—with the inferior facet of one vertebra connecting to the superior facet of an adjacent vertebra. The joints facilitate movement of the vertebra relative to each other, and allow the spine to bend and twist.

As in all synovial joints, where the facets contact each other there is a lining of cartilage lubricated by a thin layer of synovial fluid. The cartilage and synovial fluid decrease friction at the joint, extending joint life and preventing inflammation and associated pain.

As the natural aging process progresses, the cartilage covering the joint may deteriorate and start to fray. The fraying process may cause pieces of cartilage to break free, and the previously smooth surfaces may become rough. The facet bones then begin to rub together, creating friction which leads to further deterioration of the joint. Moreover, the nerves associated with the joint become irritated and inflamed, causing severe pain and restricting movement of the spine.

Techniques for addressing degeneration of synovial joints in general, and facet joints in particular, joint have heretofore relied primarily on injections to block pain and reduce inflammation. This treatment is only temporary though, and rarely leads to any significant improvement of the underlying condition.

A need therefore exists for materials and methods effective for treating degenerating synovial joints, and particularly for materials and methods effective for supplementing or replacing the cartilage that lubricates and protects the joint. The present invention addresses that need.

SUMMARY OF THE INVENTION

Briefly describing one aspect of the present invention, there is provided a method for treating synovial joints by injecting a collagen-based material into the joint. The material may be injected in a dehydrated form, and rehydrated after implantation, or it may be injected in a hydrated form, such as a slurry or gel. The material may be fresh or frozen. Crosslinking agents such as glutaraldehyde may be included in the injected material to promote collagen crosslinking. In addition, radio-contrast materials may be included to enhance imaging of the injected material. Similarly, performance-enhancing additives such as analgesics and/or antibiotics may be included to provide additional therapeutic benefits.

Objects and advantages of the claimed invention will be apparent from the following description.

BRIEF DESCRIPTION OF THE DRAWINGS

FIG.S. 1A-1D show a procedure for injecting a collagen-based material into a facet joint, according to one preferred embodiment of the present invention.

FIG.S. 2A-2F show a procedure for injecting a collagen-based material into a facet joint, according to another preferred embodiment of the present invention.

DESCRIPTION OF THE PREFERRED EMBODIMENTS

Figure 1A:
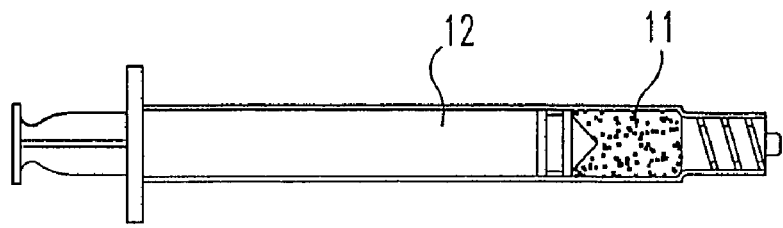

For the purposes of promoting an understanding of the principles of the invention, reference will now be made to certain preferred embodiments and specific language will be used to describe the same. It will nevertheless be understood that no limitation of the scope of the invention is thereby intended, such alterations and further modifications in the preferred embodiments being contemplated as would normally occur to one skilled in the art to which the invention relates.

As indicated above, one aspect of the present invention relates to materials and methods for using collagen-based material to treat a degenerating synovial joint. In the most preferred embodiments the collagen-based material is injected into the joint capsule. In some preferred embodiments the inventive method includes surgically adding to a synovial joint a composition comprising particulate collagen-based material. In other embodiments the inventive method includes surgically adding to a synovial joint a composition consisting essentially of particulate collagen-based material.

The collagen-based material may be derived from natural, collagen-rich tissue, such as intervertebral disc, fascia, ligament, tendon, demineralized bone matrix, etc. The material may be autogenic, allogenic, or xenogenic, or it may be of human-recombinant origin. In alternative embodiments the collagen-based material may be a synthetic, collagen-based material. Examples of preferred collagen-rich tissues include disc annulus, fascia lata, planar fascia, anterior or posterior cruciate ligaments, patella tendon, hamstring tendons, quadriceps tendons, Achilles tendons, skins, and other connective tissues.

The collagen-based material may be provided in any form appropriate for introduction into a synovial joint. For example, the material may be a solid, porous, woven, or non-woven material, and may be provided as particles, small pieces, gel, solution, suspension, paste, fibrous material, etc. The material may be used while it is still fresh and hydrated, or it may be used after having been processed, such as having been frozen and/or dehydrated.

In some embodiments the material is provided in a dehydrated state, and is "rehydrated" after injection in the joint. In other embodiments the material is implanted in a hydrated state. When the material is implanted in a hydrated state, it may be that way because it has never been dehydrated, or it may have been dehydrated and reconstituted. When reconstituted, the material may be reconstituted with saline or another aqueous medium, or it may be reconstituted with a non-aqueous medium such as ethylene glycol or another alcohol. Moreover, when provided in a "hydrated" state, the material may be provided as a gel, solution, suspension, dispersion, emulsion, paste, etc.

In the most preferred embodiments the material is a particulate and/or fibrous material suitable for injection through a hypodermic needle into a synovial joint.

In the most preferred embodiments the collagen material is provided as particles ranging between 0.05 mm and 5 mm in size. When materials such as fascia lata or disc annulus particles are used the particles preferably range in size from 0.1 mm to 5 mm. When materials such as demineralized bone matrix or gelatin are used the particles preferably range in size from 0.05 mm to 3 mm. When small plugs of material are used the plugs preferably range in size from 0.5 mm to 5 mm. In some embodiments larger sized pieces, such as pieces up to 20 mm in size, may be used.

The materials may be processed or fabricated using more than one type of tissue. For example, mixtures of fascia lata and demineralized bone matrix may be preferred in appropriate cases, as may mixtures of DBM and annulus fibrosis material.

Cross-linking agents may be added to the formulation to promote cross-linking of the collagen material. For example, glutaraldehyde or other protein cross-linking agents may be included in the formulation. The cross-linking agents may promote covalent or non-covalent crosslinks between collagen molecules. Similarly, agents to inhibit protein denaturization may also be included. Crosslinking agents that would be appropriate for use in the claimed invention are known to persons skilled in the art, and may be selected without undue experimentation.

When the material is to be used as a slurry or gel, additives to promote slurry or gel formation may also be included. These additives may promote protein folding, water binding, protein-protein interactions, and water immobilization.

In addition, a radiographic contrast media, such as barium sulfate, or a radiocontrast dye, such as sodium diatrizoate (HYPAQUE®), may be included to aid the surgeon in tracking the movement and/or location of the injected material. Radiocontrast materials appropriate for use in discography are known to persons skilled in the art, and may be selected for use in the present invention without undue experimentation.

Finally, other additives to provide benefits to the injected collagen-based material may also be included. Such additives include analgesics to reduce pain, antibiotics to minimize the potential for bacterial infection.

Polysaccharides such as proteoglycans and/or hyaluronic acid may also be included to attract and/or bind water to keep the synovial joint hydrated. Additionally, growth factors and/or other cells (e.g., intervertebral disc cells, stem cells, etc.) to promote healing, repair, regeneration and/or restoration of the joint, and/or to facilitate proper joint function, may also be included. Additives appropriate for use in the claimed invention are known to persons skilled in the art, and may be selected without undue experimentation.

In some embodiments the collagen material is dehydrated before injection into the joint, where it is rehydrated by absorbing fluid from the surrounding area. In other embodiments the collagen material is provided as a gel, slurry, or other hydrated formulation before implantation.

The collagen-based material is "surgically added" to the synovial joint. That is, the material is added by the intervention of medical personnel, as distinguished from being "added" by the body's natural growth or regeneration processes. The surgical procedure preferably includes injection through a hypodermic needle, although other surgical methods of introducing the collagen-based material into the joint may be used. For example, the material may be introduced into a synovial joint by extrusion through a dilated opening, infusion through a catheter, insertion through an opening created by trauma or surgical incision, or by other means of invasive or minimally invasive deposition of the materials into the joint space.

Figure 1B:
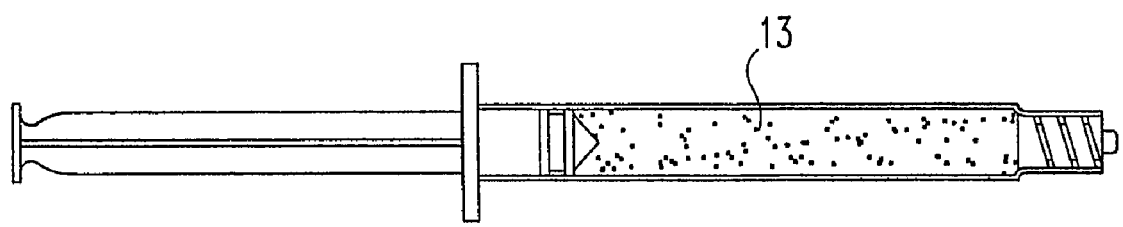
Figure 1C:
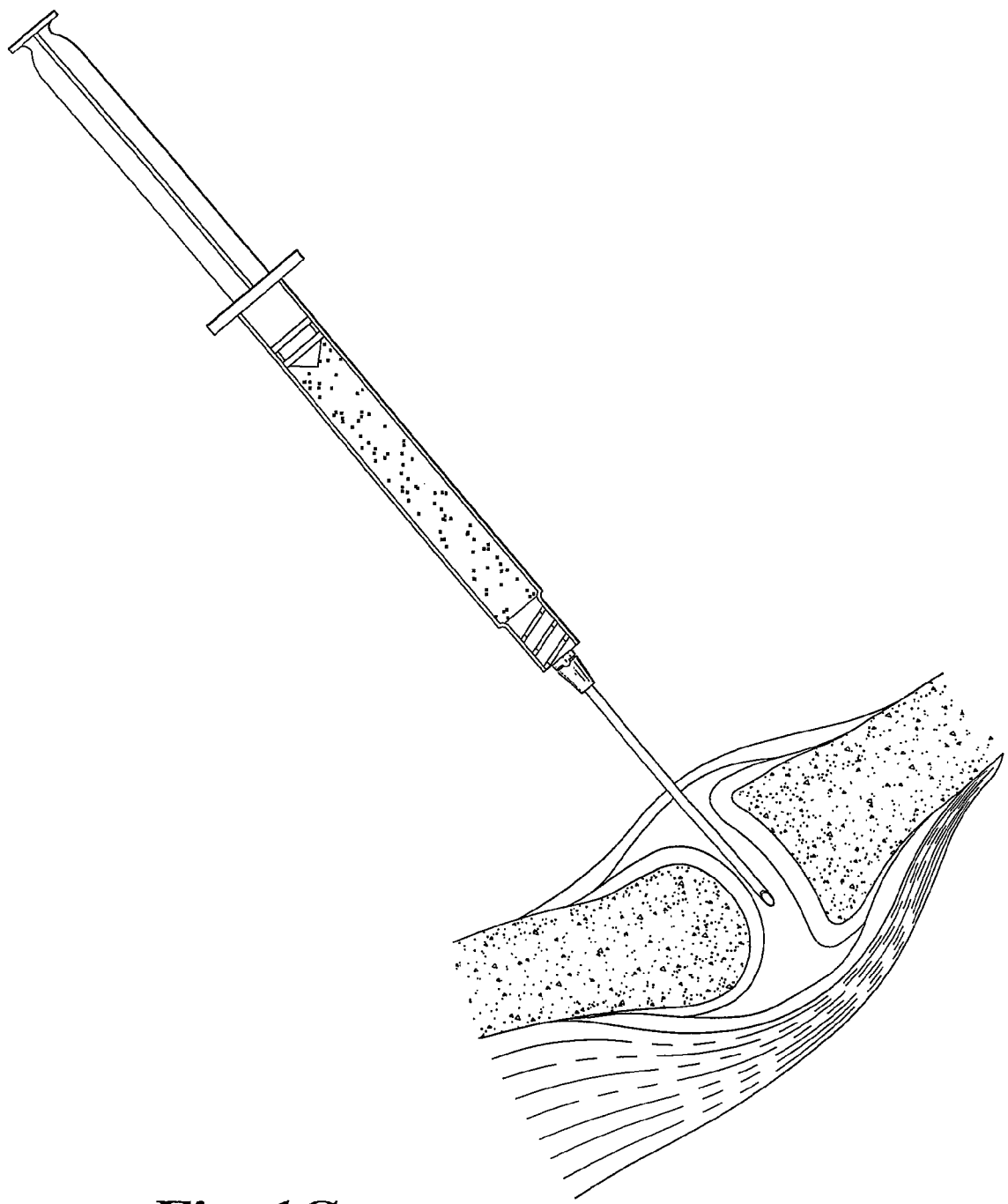
Figure 1D:
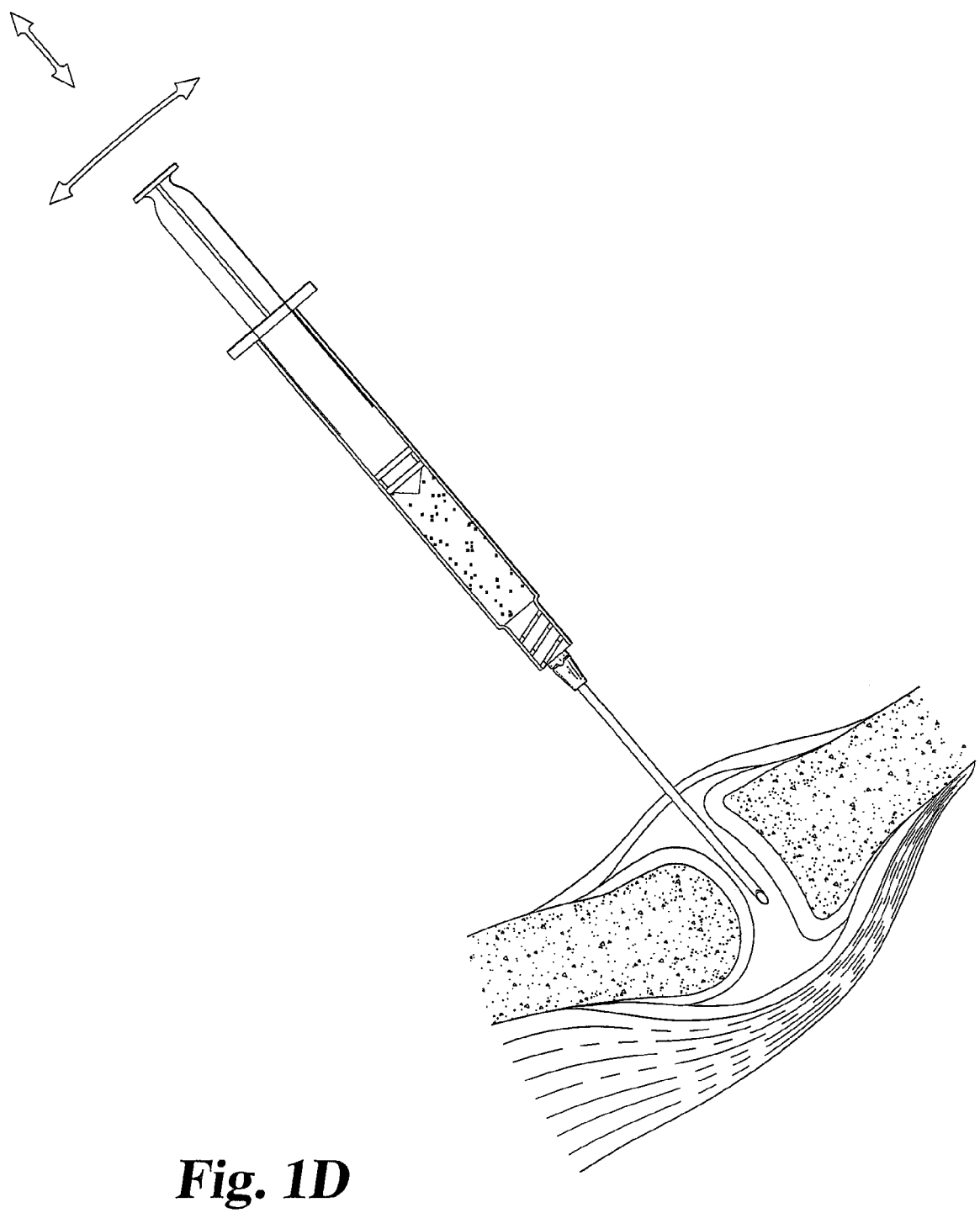

Referring now to the drawings, FIGS. 1A-1D show one method of injecting a collagen-based material into a joint. In FIG. 1A, dehydrated particulate fascia lata or annulus fibrosis material 11 is provided in a syringe 12 (in a sterile package). The material is rehydrated and/or dispersed in a suspension medium as shown in FIG. 1B, to provide a wet dispersion 13 of collagen-based material. A hypodermic needle 14 is attached to syringe 12, and the syringe is inserted into the joint capsule 16 (FIG. 1C). The needle/syringe may be moved around within the joint capsule, sweeping from side to side and back and forth, to ensure uniform distribution of the collagen-based material 13 within the space, as shown in FIG. 1D. It is preferred, however, that the tip of the needle be maintained near the center of the joint capsule to ensure deposition of the material within the space, and to minimize potential leakage.

Figure 2A:
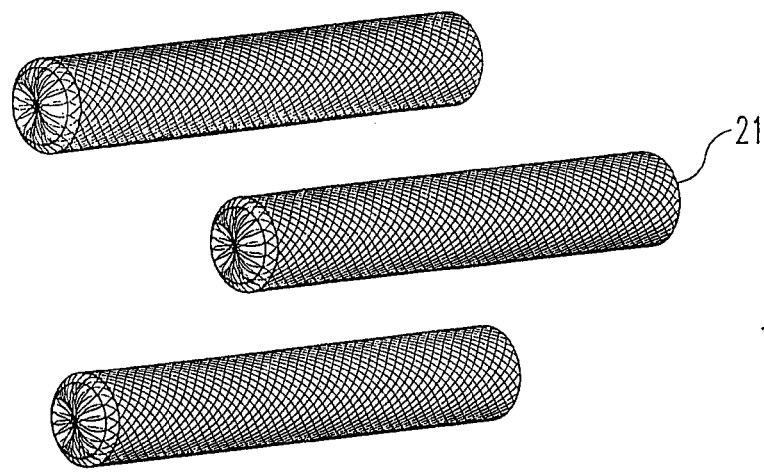
Figure 2B:
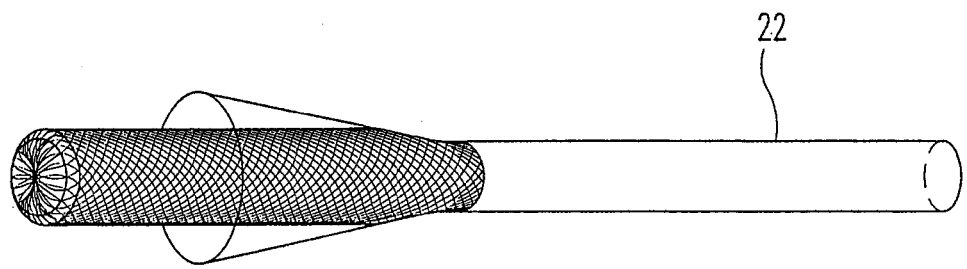
Figure 2C:

Alternatively, small diameter collagen plugs 21 may be inserted into the joint as shown in FIGS. 2A-2F. The collagen plugs 21 may be compressed before or by insertion into a small diameter tube 22, and are provided in a delivery cannula 23 (FIGS. 2A-2C). The delivery cannula 23 is attached to a dilator 24.

Figure 2D:
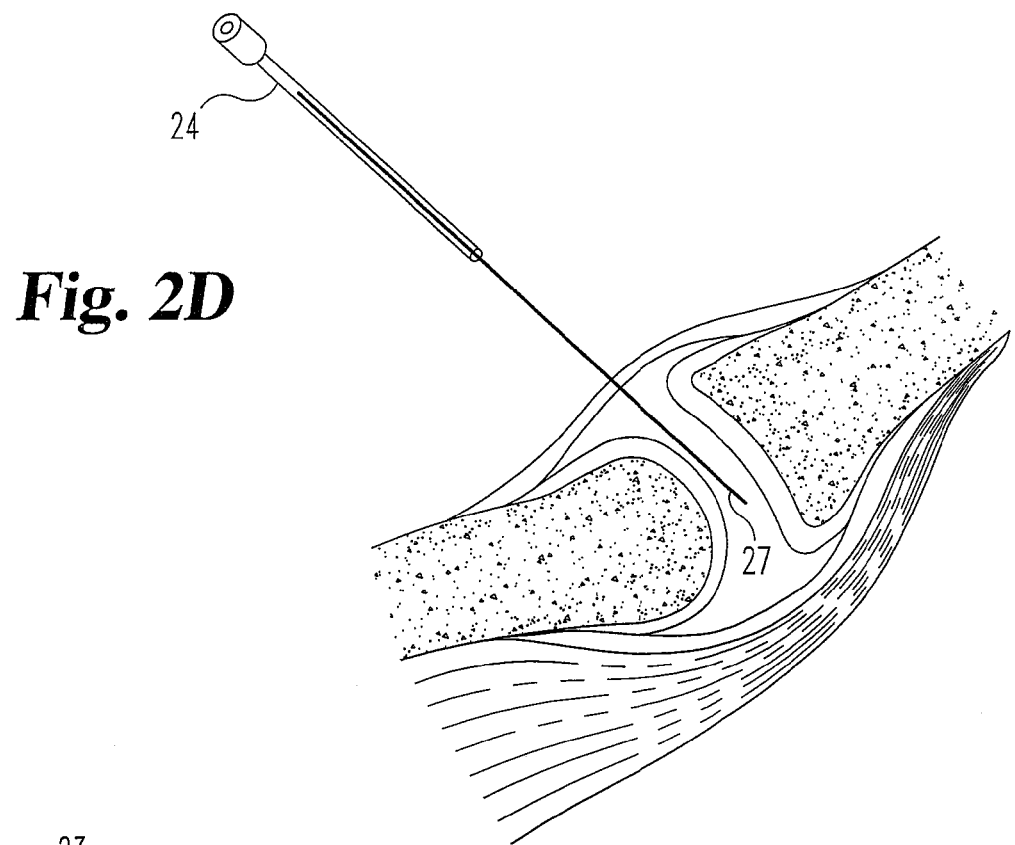
Figure 2E:
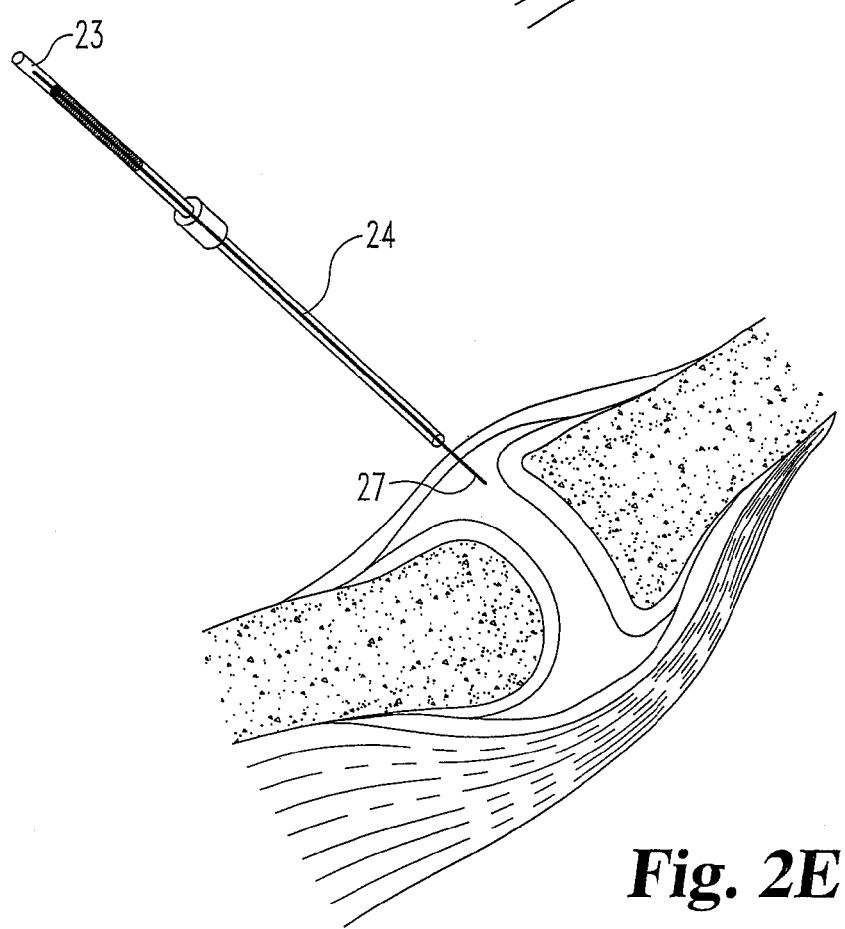
Figure 2F:
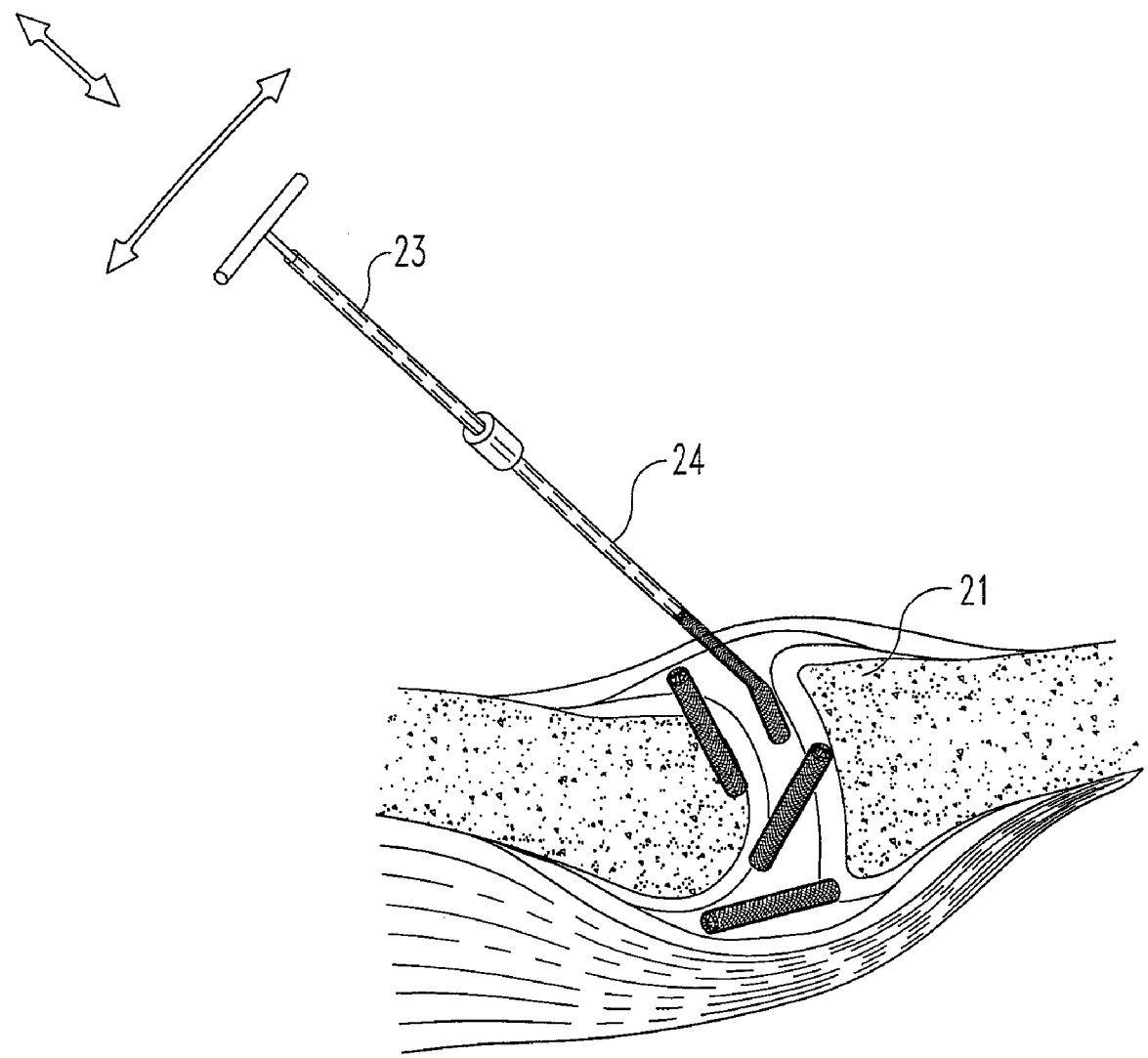

The compressed plugs are inserted into a joint 25 by penetrating the joint with a guide needle 27 (FIG. 2D). Dilator 24, preferably with delivery cannula 23 already attached, is inserted over guide needle 27 (FIG. 2E). The collagen plugs 21 are then ready for injection (or extrusion) into the joint. A plunger 28 may be used to push the plugs from the cannula. The plugs expand upon exiting the dilator, and may further expand as they rehydrate in the joint.

Benefits and advantages arising from use of the materials and methods of the present invention include the following:
 (1) the invention provides lubrication and/or cushioning to degenerated synovial joints, improving or restoring proper joint function;
 (2) the rehydration provided by the invention is expected to slow the degenerative process;
 (3) the invention relieves pain due to improved lubrication of the joint;
 (4) the procedure is percutaneous or a minimally invasive outpatient procedure;
 (5) the risks are minimal, as similar techniques and materials are used in cosmetic procedures;
 (6) the materials are biocompatible since natural or human-recombinant collagen-based materials are used;

In one preferred embodiment the materials and methods of the present invention may be used to treat synovial joints in the spine, particularly facet joints. In other preferred embodiments hip, knee, ankle, finger, toe, elbow, shoulder, wrist, sacroiliac, temporomandibular, carpometacarpal, etc., joints may all be treated by injecting a collagen-source material into the joint space to supplement/augment the cartilage that lubricates the joint.

Reference will now be made to specific examples using the processes described above. It is to be understood that the examples are provided to more completely describe preferred embodiments, and that no limitation to the scope of the invention is intended thereby.

EXAMPLE 1

A gel or suspension of hydrated particulate or fibrous (autologous or allogenic) fascia lata in a biocompatible medium such as water, saline, or ethylene glycol is used to supplement the cartilage of a facet joint. The particle size can be in the range from 0.01 mm to 5 mm, preferably between 0.05 and 0.25 mm. The suspension is injected directly into the articular facet joint space through an intact joint capsule using a hypodermic needle. The suspension is contained within the joint capsule following injection. The medium subsequently diffuses out of the disc space and leaves the hydrated fascia lata material behind. A single injection is effective for improving the facet joint structure, although additional injections may be necessary to achieve appropriate level of treatment.

EXAMPLE 2

A gel or suspension of hydrated particulate or fibrous allogenic annulus fibrosis in a biocompatible medium such as water, saline or ethylene glycol is used to supplement the cartilage of a facet joint. The particle size can be in the range from 0.01 mm to 5 mm, preferably between 0.05 and 0.25 mm. The suspension is injected directly into the articular facet joint space through an intact joint capsule using a hypodermic needle. The suspension is contained within the joint capsule following injection. The medium subsequently diffuses out of the disc space and leaves the hydrated annulus fibrosis material behind. Single injection is desirable; however, additional injections may be necessary to achieve the appropriate level of treatment.

EXAMPLE 3

Dehydrated annulus fibrosis material in granule, particulate or power form is used to supplement the cartilage of a facet joint. The particle size can range between 0.01 mm and 5 mm, preferably between 0.05 to 0.25 mm. The material is loaded in its dehydrated state into a specially designed syringe for delivery of particulate matter. The material is extruded into the articular facet joint space through a small, dilated capsule opening. The material remains inside the articulating facet joint space after the needle is removed. It subsequently absorbs moisture or body fluids and swells up in vivo.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A method of treating a synovial joint, said method comprising surgically adding to a synovial joint a composition consisting essentially of particulate collagen-based material.

2. The method of claim 1 wherein said surgically adding step comprises injecting particulate collagen-based material into a synovial joint.

3. The method of claim 1 wherein said collagen-based material comprises particles ranging from 0.05 mm to 5 mm in size.

4. The method of claim 1 wherein said collagen-based material comprises particles ranging from 0.05 mm to 3 mm in size.

5. The method of claim 1 wherein said collagen-based material comprises particles ranging from 0.05 mm to 1 mm in size.

6. The method of claim 1 wherein said collagen-based material comprises particles ranging from 0.25 mm to 1 mm in size.

7. The method of claim 1 wherein said collagen-based material is injected in a dehydrated state.

8. The method of claim 1 wherein said collagen-based material is injected in a non-dehydrated state.

9. The method of claim 8 wherein said collagen-based material is injected as a gel.

10. The method of claim 8 wherein said collagen-based material is injected as a solution or suspension.

* * * * *